US00PP15738P2

(12) United States Plant Patent
Lim et al.

(10) Patent No.: US PP15,738 P2
(45) Date of Patent: Apr. 26, 2005

(54) SHRUB ROSE PLANT NAMED 'BAIOIST'

(50) Latin Name: *Rosa hybrida*
Varietal Denomination: BAIoist

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 39 days.

(21) Appl. No.: 10/811,997

(22) Filed: Mar. 30, 2004

(51) Int. Cl.[7] ..... A01H 5/00
(52) U.S. Cl. ..... Plt./102
(58) Field of Search ..... Plt./102

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of landscape shrub rose plant is provided which forms on a continuous basis in clusters attractive vibrant double red-orange blossoms with light rosy-orange on the under surface of the recurved petals. The plant exhibits a compact, upright and bushy growth habit, satiny medium green foliage, and excellent tolerance to Black Spot and Powdery Mildew. The attractive medium green glossy foliage contrasts nicely with the red-orange blossom coloration. A tough rose plant of good hardiness is provided. The plant can be grown to advantage as a specimen, border planting, or as a mass planting.

2 Drawing Sheets

Botanical commercial classification: *Rosa hybrida*/Shrub Rose Plant.
Varietal denomination: cv. 'BAIoist'.

SUMMARY OF THE INVENTION

The new variety of *Rosa hybrida* landscape shrub rose plant was created at Yamhill, Oreg. during 1993 by artificial pollination wherein two parents were crossed which previously had been studied in the hope that they would contribute the desired characteristics. The female parent (i.e., the seed parent) was an unnamed plant designated 4-40A. Such female parent was an unreleased plant from our breeding program and was not available to the public. The male parent (i.e., the pollen parent) was the 'Meipoque' variety (U.S. Plant Pat. No. 5,956). The 'Meipoque' variety is marketed under the PINK MEIDILAND trademark. The parentage of the new variety can be summarized as follows:

4-40Ax'Meipoque'.

The seeds resulting from the above pollination were sown and plants were obtained which were physically and biologically different from each other. Selective study resulted in the identification during 1995 of a single plant of the new variety having the distinctive ornamental characteristics hereafter described.

It was found that the new variety of the present invention:

(a) exhibits a compact, upright and bushy growth habit,
(b) forms continuously in clusters attractive vibrant double red-orange blossoms with light rosy-orange on the under surface of the recurved petals,
(c) forms satiny medium green adult foliage,
(d) displays excellent tolerance to Black Spot and Powdery Mildew; and
(e) is particularly well suited for growing as attractive ornamentation in parks and gardens.

The orange-red blossoms contrast nicely with the satiny medium green glossy foliage. The official American Rose Society blossom color is orange. A tough shrub rose plant having good hardiness is provided.

The new variety well meets the needs of the horticultural industry. It can be grown to advantage anywhere in the landscape where attractive ornamentation is desired. The distinctive blossoms are displayed throughout the summer on a recurrent bloom cycle. The plant can be grown as a specimen, border planting, or as a mass ground cover.

The new variety can be readily distinguished from other varieties including its parental varieties. More specifically, the 4-40A plant forms deep orange double blossoms having approximately 30 petals on average and commonly assumes a greater plant height of approximately 1.25 m, and the 'Meipoque' variety forms single pink blossoms with a white center having approximately 5 petals on average and commonly assumes a greater plant height of approximately 1.5 m. The 'Morden Fireglow' variety (U.S. Plant Pat. No. 8,060) forms ovoid buds, dark red opening flowers, smaller red-orange fully open flowers having a diameter of approximately 7.5 cm, and commonly assumes a lesser plant height of approximately 80 cm. The 'AUSmum' variety (U.S. Plant Pat. No. 9,527) forms pointed buds, very double orange-red opening flowers having approximately 50 petals, larger orange-red with a yellow-orange reverse fully open flowers having a diameter of approximately 10 cm, and commonly assumes a greater plant height of approximately 1.5 m.

The new variety has been found to undergo asexual propagation by budding on an understock beginning in April 1994 and by the rooting of cuttings. 'Dr. Huey' rootstock was used during the budding. Such asexual propagation by these techniques at Yamhill, Oreg. and at Phoenix, Ariz. has shown that the characteristics of the new variety are stable and are strictly transmissible by such asexual propagation from one generation to another. The new variety grows well on its own roots.

Initially the new plant was designated 93A135-1T. The new variety subsequently has been named the 'BAIoist' variety, and currently is being marketed while using the GARDEN ART and ORANGE IMPRESSIONIST trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately three years of age, and were being grown outdoors at Yamhill, Oreg. during the 2002 season.

DETAILED DESCRIPTION

Figure 1:
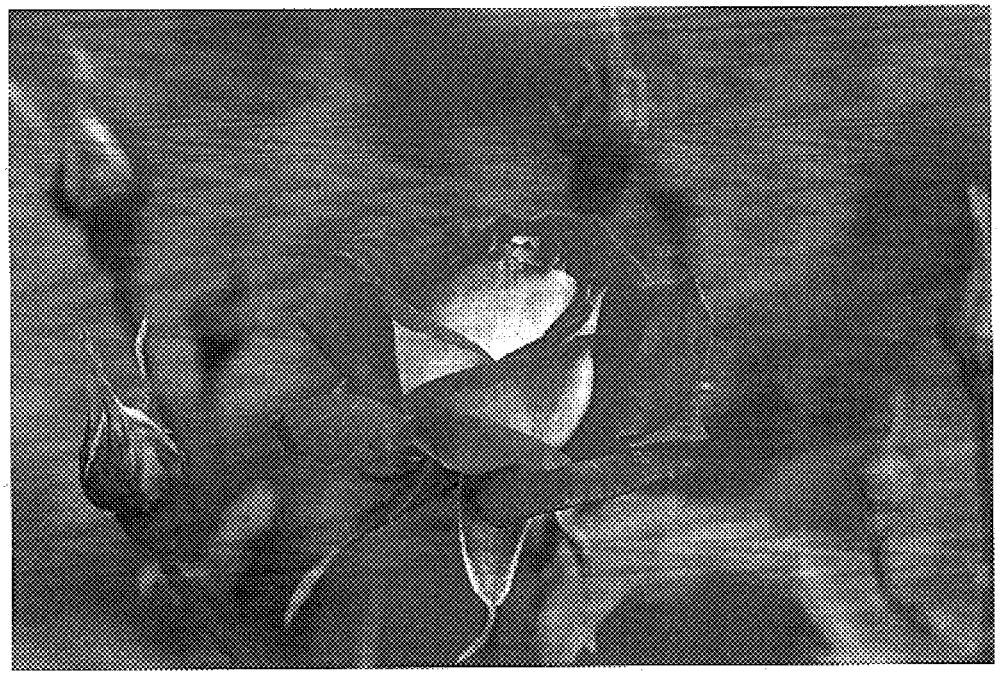
FIG. 1 illustrates typical newly-opened blossom and buds of the new variety. The light rosy-orange coloration on the under surface of the petals is included.
Figure 2:
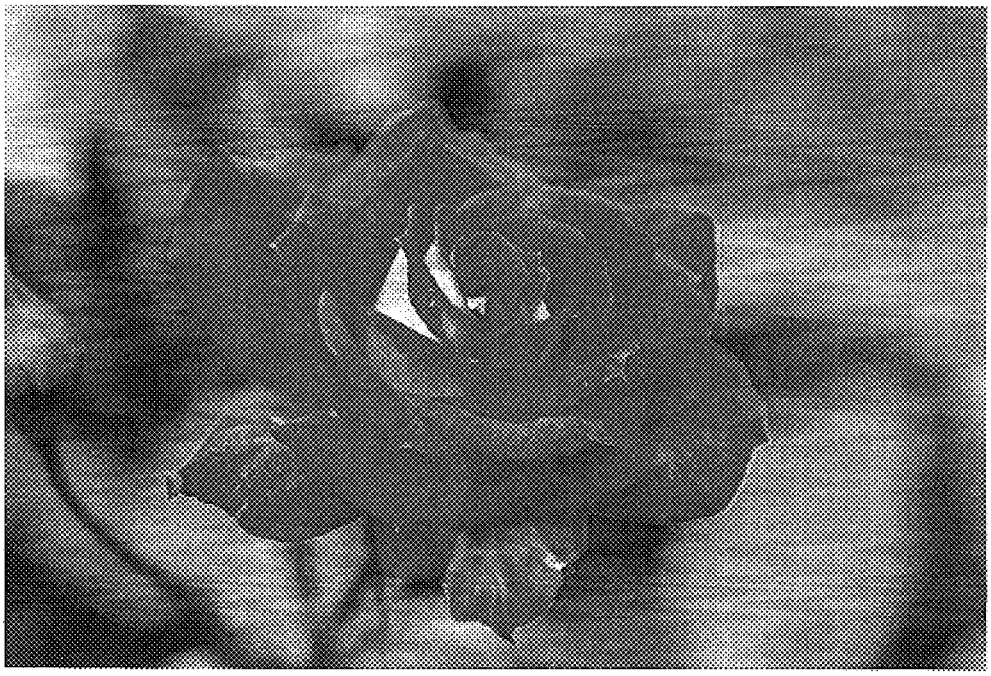
FIG. 2 illustrates a typical blossom of the new variety in a more advanced stage of opening.
Figure 3:
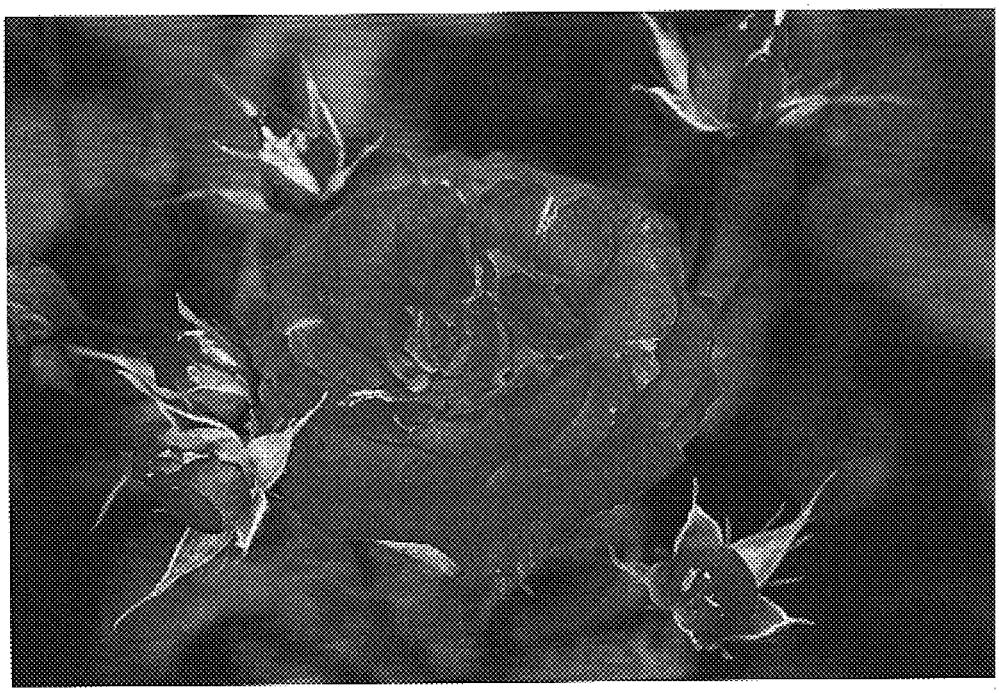
FIG. 3 illustrates an additionally fully opened blossom of the new variety as well as a cluster of buds. The sepals with small foliaceous appendages also are shown.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2003, at St. Paul, Minn., and at Yamhill, Oreg.

Botanical classification: *Rosa hybrida,* var. 'BAIoist'.
Class: Landscape Shrub.
Plant:
- *Height.*—Approximately 90 cm on average at the end of the growing season.
- *Width.*—Approximately 80 cm on average at the end of the growing season.
- *Habit.*—Compact, dense, upright, bushy, and rounded.

Branches:
- *Color.*—Young stems: Yellow-Green Group 144A and 144B with highlights of Red Group 46A. Adult wood: Yellow-Green Group 146C suffused with Greyed-Purple Group 184B.
- *Thorns.*—Size: commonly approximately 0.5 cm in length on average. Color: Greyed-Purple Group 184C and 184D.

Leaves:
- *Stipules.*—Generally parallel with the auricle facing outward.
- *Petioles.*—Upper surface: between Yellow-Green Group 146A and 146B with highlights of Greyed-Purple Group 183B. Under surface: Yellow-Green Group 146D.
- *Leaflets.*—Number: 3, 5 (most often), and 7. Shape: ovate with a rounded base and an acuminate tip. Margin: serrulate. Texture: bears a satiny finish and is physically firm. General appearance: dense, medium green with a satiny surface when mature. Color (young foliage): Upper surface: between Greyed-Purple Group 187A and 187B. Under surface: Greyed-Purple Group 187A. Color (adult foliage): Upper surface: between Green Group 137B and Yellow-Green Group 146A. Under surface: between Yellow-Green Group 146B and Yellow-Green Group 147B.

Inflorescence:
- *Number of flowers.*—Commonly approximately 8 blooms on average per cluster on a lateral stem.
- *Peduncle.*—Yellow-Green Group 144C and Yellow-Green Group 148A with highlights of Greyed-Purple Group 184A in coloration, and the length is approximately 5.0 cm on average.
- *Sepals.*—Upper surface: Yellow-Green Group 144A suffused with between Greyed-Purple Group 184A and 184B and with some pubescence. Under surface: Yellow-Green Group 144A and 144B and mottled with Greyed-Purple Group 187C. Size: approximately 2.75 cm in length on average.
- *Buds.*—Shape: generally rounded. Size: medium. Length: approximately 1.75 cm on average. Diameter: approximately 1.25 cm on average. Color: Upper petal surface: Red Group 43A and 43B. Under petal surface: Red Group 36A and 36B with highlights of Red Group 43D at the margin.
- *Flower.*—Shape: double, and resembles that of a Tea Rose. Diameter: approximately 8.75 cm on average. Color (when opening begins): upper surface: between Red Group 43A and 43B. Under surface: Red Group 51D with Red Group 43B on the edge. Color (when blooming): Upper surface: between Red Group 43A and 43B blending with Red Group 49C and Red Group 48A towards the basal petal spot. Under surface: between Red Group 49B and Red Group 50D. Color (at end of blooming): Upper surface: an irregular blending of Red Group 50A, 50B, and 50C suffused with Red Group 59D. Under surface: between Red Group 49B and 50D. Color (basal petal spot): Yellow-White Group 158D. Fragrance: slight spice. Lasting quality: the blossoms commonly last approximately 4 to 6 days on average depending upon the temperature and sunlight exposure, and when in a vase approximately 4 to 5 days if cut when the buds are opening. Petal number: approximately 30 under normal growing conditions. Petal shape: wedge-shaped with a curled apex. Petal drop: commonly the petals detach cleanly at full blossom maturity. Anthers: Yellow-Orange Group 21B. Filament number: commonly approximately 86 on average. Filament color: Yellow Group 12B. Pistils: approximately 46 on average. Stigmas: Greyed-Yellow Group 161A in coloration. Styles: Greyed-Yellow Group 160D in coloration. Receptacle: separate and free with achenes on the bottom and center. Hip shape: ovoid. Seeds: oval, rugose at the apex with villose hairs, and Greyed-Orange Group 165C with streaks of Greyed-Orange Group 166A in coloration.

Development:
- *Vegetation.*—Dense, and compact.
- *Blooming.*—Heavy in June and continuously thereafter.
- *Resistance to diseases.*—Excellent tolerance to Black Spot, and Powdery Mildew.
- *Hardiness zone.*—U.S.D.A. Hardiness Zone Nos. 5 to 9. With some protection the variety has been satisfactorily grown at St. Paul, Minn.

We claim:

1. A new and distinct variety of landscape shrub rose plant characterized by the following combination of characteristics:

(a) exhibits a compact, upright and bushy growth habit, (b) forms continuously in clusters attractive vibrant double red-orange blossoms with light rosy-orange on the under surface of the recurved petals, (c) forms satiny medium green adult foliage, (d) displays excellent tolerance to Black Spot and Powdery Mildew; and (e) is particularly well suited for growing as attractive ornamentation in parks and gardens;

substantially as herein shown and described.

* * * * *